(12) United States Patent
Brodbeck et al.

(10) Patent No.: US 6,331,311 B1
(45) Date of Patent: Dec. 18, 2001

(54) INJECTABLE DEPOT GEL COMPOSITION AND METHOD OF PREPARING THE COMPOSITION

(75) Inventors: Kevin J. Brodbeck, Palo Alto; Theodore T. Shen, Redwood City, both of CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 08/993,031

(22) Filed: Dec. 18, 1997

Related U.S. Application Data

(60) Provisional application No. 60/033,439, filed on Dec. 20, 1996.

(51) Int. Cl.[7] ............... A61F 2/00; A61K 9/14
(52) U.S. Cl. ............ 424/425; 424/423; 424/426; 424/486
(58) Field of Search ................. 424/423, 425, 424/426, 486, 501, 871.1

(56) References Cited

U.S. PATENT DOCUMENTS

| | | | |
|---|---|---|---|
| 3,792,010 | 2/1974 | Wasserman et al. | 260/32.2 R |
| 3,923,939 | 12/1975 | Baker et al. | 264/49 |
| 4,675,189 | 6/1987 | Kent et al. | 424/490 |
| 4,938,763 | 7/1990 | Dunn et al. | 604/891.1 |
| 4,962,091 | 10/1990 | Eppstein et al. | 514/2 |
| 4,981,696 | 1/1991 | Loomis et al. | 424/423 |
| 5,019,400 | 5/1991 | Gombotz et al. | 424/497 |
| 5,077,049 | 12/1991 | Dunn et al. | 424/426 |
| 5,085,866 | 2/1992 | Consar et al. | 424/481 |
| 5,192,741 | 3/1993 | Orsolini et al. | 514/4 |
| 5,229,422 * | 7/1993 | Takahashi et al. | 514/558 |
| 5,242,910 | 9/1993 | Damanj | 514/152 |
| 5,278,201 | 1/1994 | Dunn et al. | 523/113 |
| 5,278,202 | 1/1994 | Dunn et al. | 523/113 |
| 5,292,782 | 3/1994 | Bastioli et al. | 524/47 |
| 5,318,780 | 6/1994 | Viegas et al. | 424/427 |
| 5,324,519 | 6/1994 | Dunn et al. | 424/426 |
| 5,340,849 | 8/1994 | Dunn et al. | 523/113 |
| 5,358,475 | 10/1994 | Mares et al. | 623/66 |
| 5,368,859 | 11/1994 | Dunn et al. | 424/426 |
| 5,447,725 | 9/1995 | Damani et al. | 424/435 |
| 5,487,897 | 1/1996 | Poison et al. | 424/426 |
| 5,525,646 | 6/1996 | Lundren et al. | 523/105 |
| 5,556,905 | 9/1996 | Frappier et al. | 524/311 |
| 5,599,552 | 2/1997 | Dunn et al. | 424/423 |
| 5,620,700 | 4/1997 | Berggren et al. | 424/435 |
| 5,632,727 | 5/1997 | Tipton et al. | 602/47 |
| 5,633,002 | 5/1997 | Stricker et al. | 424/426 |
| 5,650,173 | 7/1997 | Ramstack et al. | 424/489 |
| 5,654,010 | 8/1997 | Johnson et al. | 424/502 |
| 5,656,297 | 8/1997 | Bernstein et al. | 424/484 |
| 5,660,849 | 8/1997 | Polson et al. | 424/426 |
| 5,667,808 | 9/1997 | Johnson et al. | 424/501 |
| 5,674,534 | 10/1997 | Zale et al. | 424/501 |
| 5,681,873 | 10/1997 | Norton et al. | 523/115 |
| 5,702,716 | 12/1997 | Dunn et al. | 424/422 |
| 5,702,717 * | 12/1997 | Cha et al. | 424/425 |
| 5,707,647 | 1/1998 | Dunn et al. | 424/443 |
| 5,711,968 | 1/1998 | Tracy et al. | 424/487 |
| 5,716,644 | 2/1998 | Zale et al. | 424/497 |
| 5,717,030 | 2/1998 | Dunn et al. | 523/111 |
| 5,725,491 | 3/1998 | Tipton et al. | 602/43 |
| 5,733,566 | 3/1998 | Lewis | 424/426 |
| 5,733,567 | 3/1998 | Arola et al. | 424/426 |
| 5,733,950 | 3/1998 | Dunn et al. | 523/113 |
| 5,736,152 | 4/1998 | Dunn et al. | 424/426 |
| 5,739,176 | 4/1998 | Dunn et al. | 523/113 |
| 5,744,153 | 4/1998 | Yewey et al. | 424/426 |
| 5,759,563 | 6/1998 | Yewey et al. | 424/426 |
| 5,780,044 | 7/1998 | Yewey et al. | 424/426 |
| 5,792,469 | 8/1998 | Tipton et al. | 424/422 |

FOREIGN PATENT DOCUMENTS

| | | | |
|---|---|---|---|
| 3635679 A1 | 5/1988 | (DE) | A61L/17/00 |
| 0 539 751 A1 | 5/1993 | (EP) | A61K/9/00 |
| 0 640 647 A2 | 3/1995 | (EP) | C08L/5/08 |
| WO 90/03768 | 4/1990 | (WO) | A61F/2/00 |
| WO 91/05544 | 5/1991 | (WO) | A61K/9/00 |
| WO 92/00718 | 1/1992 | (WO) | A61K/6/00 |
| WO 93/20134 | 10/1993 | (WO) | C08K/5/00 |
| WO 95/27481 | 10/1995 | (WO) | A61K/9/22 |
| WO 96/21427 | 7/1996 | (WO) | A61K/9/00 |
| WO 97/15285 | 5/1997 | (WO) | A61K/9/00 |
| WO 97/15287 | 5/1997 | (WO) | A61K/9/10 |
| WO 98/07412 | 2/1998 | (WO) | A61K/9/16 |

OTHER PUBLICATIONS

Yewey, G. L. Duysen, E. G., Cox, S. M., and Dunn, R. L., Chapter 3, "Delivery of Proteins from a Controlled Release Injectable Implant," pp. 93–117, Protein Delivery: Physical Systems, Sanders and Hendren, eds., Plenum Press, New York, 1997.

Modern Plastics Encyclopedia, pp. C99–C109, mid–November, 1996.

Nema, S., Washkuhn, R. J., and Brendel, R. J., "Excipients and Their Use in Injectable Products," PDA J. Pharm. Sci. Technol. (United States) Jul.–Aug. 1997, 51 (4), pp. 166–171.

Scotchford, C. A., et al., "Water uptake and protein release characteristics of a new methacrylate–based polymer system," Polymer, vol. 38, No. 15, pp. 3869–3874, 1997.

(List continued on next page.)

Primary Examiner—Theodore J. Criares
(74) Attorney, Agent, or Firm—Vandana Bate

(57) ABSTRACT

An injectable depot gel composition containing a polymer, a solvent that can dissolve the polymer and thereby form a viscous gel, a beneficial agent; and an emulsifying agent in the form of a dispersed droplet phase in the viscous gel. The injectable depot gel composition can be prepared by mixing the polymer and the solvent so that the solvent dissolves the polymer and forms a viscous gel. The beneficial agent is dissolved or dispersed in the viscous gel and the emulsifying agent is mixed with the beneficial agent containing viscous gel. The emulsifying agent forms a dispersed droplet phase in the viscous gel to provide the injectable depot gel composition. The injectable depot gel composition can deliver a beneficial agent to a human or animal with a desired release profile.

27 Claims, 3 Drawing Sheets

OTHER PUBLICATIONS

Johnson, M. L., Jaworowicz, W., Cleland J. L., Bailey, L., Charnis, M., Duenas, E., Wu, C., Shepard, D., Magil, S., Last, T., Jones, A.J.S., and Putney, S. D., "The Stabilization and Encapsulation of Human Growth Hormone into Biodegradable Microspheres," Pharm. Res., vol. 14, No. 6, 1997.

Search Report of WO 98/27962, filed Jul. 2, 1998, published Oct. 1, 1998, Brodbeck, K. J., et al.

Search Report of WO 98/27963, filed Jul. 2, 1998, published Oct. 15, 1998, Brodbeck, K. J., et al.

Cunningham, B. C., Mulkerrin, M. G., Wells, J. A., "Dimerization of Human Growth Hormone by Zinc," Science, vol. 253, pp. 545–548, 1991.

Derwent Abstract (English language) of DE 3635679 A (listed in Foreign Documents above).

Sato, T., Kanke, M., Schroeder, H. G., and DeLuca, P.P., "Porous Biodegradable Microspheres for Controlled Drug Delivery. I. Assessment of Processing Conditions and Solvent Removal Techniques," Pharm. Res. vol. 5, No. 1, pp. 21–30, 1997.

Zhang, Y., Zale, S., Sawyer, L., and Bernstein, H., "Effects of metal salts on poly(DL–lactide–co–glycolide) polymer hydrolysis", J. Biomedical Materials Research, vol. 34, 531–538, 1997.

* cited by examiner

INJECTABLE DEPOT GEL COMPOSITION AND METHOD OF PREPARING THE COMPOSITION

This application claims the priority of provisional application Serial No. 60/033,439, filed Dec. 20, 1996, which is incorporated herein by reference.

BACKGROUND OF THE INVENTION

1. Field of the Invention

The present invention relates to a depot gel composition that can be injected into a desired location and which can provide sustained release of a beneficial agent. The present invention also relates to a method of preparing the composition.

2. Description of the Related Art

Biodegradable polymers have been used for many years in medical applications. Illustrative devices composed of the biodegradable polymers include sutures, surgical clips, staples, implants, and drug delivery systems. The majority of these biodegradable polymers have been based upon glycolide, lactide, caprolactone, and copolymers thereof.

The biodegradable polymers can be thermoplastic materials which means that they can be heated and formed into various shapes such as fibers, clips, staples, pins, films, etc. Alternatively, they can be thermosetting materials formed by crosslinking reactions which lead to high-molecular-weight materials that do not melt or form flowable liquids at high temperatures.

Although thermoplastic and thermosetting biodegradable polymers have many useful biomedical applications, there are several important limitations to their use in the bodies of various animals including humans, animals, birds, fish, and reptiles. Because these polymers are solids, all instances involving their use have required initially forming the polymeric structures outside the body, followed by insertion of the solid structure into the body. For example, sutures, clips, and staples are all formed from thermoplastic biodegradable polymers prior to use. When inserted into the body, they retain their original shape. While this characteristic is essential for some uses, it is a drawback where it is desired that the material flow to fill voids or cavities where it may be most needed.

Drug delivery systems using thermoplastic or thermosetting biodegradable polymers also have to be formed outside the body. In such instances, the drug is incorporated into the polymer and the mixture is shaped into a certain form such a cylinder, disc, or fiber for implantation. With such solid implants, the drug delivery system has to be inserted into the body through an incision. These incisions are sometimes larger than desired by the medical profession and occasionally lead to a reluctance of the patients to accept such an implant or drug delivery system. Nonetheless, both biodegradable and non-biodegradable implantable drug delivery systems have been widely used successfully.

One reservoir device having a rate-controlling membrane and zero-order release of an agent that is particularly designed for intraoral implantation is described in U.S. Pat. No. 5,085,866. The device is prepared from a core that is sprayed with a solution having a polymer and a solvent that is composed of a rapidly evaporating, low boiling point first solvent and a slowly evaporating, high boiling second solvent.

Other illustrative osmotic delivery systems include those disclosed in U.S. Pat. Nos. 3,797,492, 3,987,790, 4,008,719, 4,865,845, 5,057,318, 5,059,423, 5,112,614, 5,137,727, 5,151,093, 5,234,692, 5,234,693, 5,279,608, and 5,336,057. Pulsatile delivery devices are also known which deliver a beneficial agent in a pulsatile manner as disclosed in U.S. Pat. Nos. 5,209,746, 5,308,348, and 5,456,679.

One way to avoid the incision needed to implant drug delivery systems is to inject them as small particles, microspheres, or microcapsules. For example, U.S. Pat. No. 5,019,400 describes the preparation of controlled release microspheres via a very low temperature casting process. These materials may or may not contain a drug which can be released into the body. Although these materials can be injected into the body with a syringe, they do not always satisfy the demand for a biodegradable implant. Because they are particulate in nature, they do not form a continuous film or solid implant with the structural integrity needed for certain prostheses. When inserted into certain body cavities such as a mouth, a periodontal pocket, the eye, or the vagina where there is considerable fluid flow, these small particles, microspheres, or microcapsules are poorly retained because of their small size and discontinuous nature. Further, the particles tend to aggregate and thus their behavior is hard to predict. In addition, microspheres or microcapsules prepared from these polymers and containing drugs for release into the body are sometimes difficult to produce on a large scale, and their storage and injection characteristics present problems. Furthermore, one other major limitation of the microcapsule or small-particle system is their lack of reversibility without extensive surgical intervention. That is, if there are complications after they have been injected, it is considerably more difficult to remove them from the body than with solid implants. A still further limitation on microparticles or microcapsulation is the difficulty in encapsulating protein and DNA-based drugs without degradation caused by solvents and temperature extremes.

The art has developed various drug delivery systems in response to the aforementioned challenges. For instance, U.S. Pat. No. 4,938,763 and its divisional U.S. Pat. No. 5,278,201 relate to a biodegradable polymer for use in providing syringeable, in-situ forming, solid biodegradable implants for animals. In one embodiment, a thermoplastic system is used wherein a non-reactive polymer is dissolved in a biocompatible solvent to form a liquid which is placed in the animal wherein the solvent dissipates to produce the solid implant. Alternatively, a thermosetting system is used wherein effective amounts of a liquid acrylic esterterminated, biodegradable prepolymer and a curing agent are formed and the liquid mixture is placed within the animal wherein the prepolymer cures to form the solid implant. It is stated that the systems provide a syringeable, solid biodegradable delivery system by the addition of an effective level of a biologically active agent to the liquid before the injection into the animal.

U.S. Pat. No. 5,242,910 describes a sustained release composition for treating periodontal disease. The composition comprises copolymers of lactide and glycolide, triacetin (as a solvent/plasticizer) and an agent providing relief of oral cavity diseases. The composition can take the form of a gel and can be inserted into a periodontal cavity via a syringe using either a needle or a catheter. As additional optional components, the composition can contain surfactants, flavoring agents, viscosity controlling agents, complexing agents, antioxidants, other polymers, gums, waxes/oils, and coloring agents. One illustrative viscosity controlling agent set forth in one of the examples is polyethylene glycol 400.

With solvent-based depot compositions comprised of a polymer dissolved in a solvent, one problem which exists is that the composition solidifies slowly after injection as solvent diffuses from the depot. Since these compositions need to be non-viscous in order to be injected, a large percentage of drug is released as the system forms by diffusion of the solvent. This effect is referred to as a "burst" effect. In this respect, it is typical for solvent-based compositions to have a drug burst wherein 30–75% of the drug contained in the composition is released within one day of the initial injection.

SUMMARY OF THE INVENTION

The present invention is a significant advance in the art and in one aspect provides an injectable depot gel composition comprising:

A) a biocompatible polymer;
B) a solvent that dissolves the polymer and forms a viscous gel;
C) a beneficial agent; and
D) an emulsifying agent in the form of a dispersed droplet phase in the viscous gel.

In a further aspect, the present invention provides a method of preparing an injectable depot gel composition comprising:

A) mixing a biocompatible polymer and a solvent whereby the solvent dissolves the polymer and forms a viscous gel;
B) dispersing or dissolving a beneficial agent in the viscous gel to form a beneficial agent containing gel; and
C) mixing an emulsifying agent with the beneficial agent containing gel, said emulsifying agent forming a dispersed droplet phase in the beneficial agent containing gel so as to provide the injectable depot gel composition.

In another aspect, the present invention provides a method of preparing an injectable depot gel composition comprising:

A) mixing a biocompatible polymer and a solvent whereby the solvent dissolves the polymer and forms a viscous gel;
B) dispersing or dissolving a beneficial agent in an emulsifying agent to form a beneficial agent containing emulsifying agent; and
C) mixing the beneficial agent containing emulsifying agent with the viscous gel, said beneficial agent containing emulsifying agent forming a dispersed droplet phase in the viscous gel to provide the injectable depot gel composition.

In yet another aspect, the invention provides an injectable depot gel composition comprising:

A) a biocompatible polymer;
B) a solvent that dissolves the polymer and forms a viscous gel; and
C) an emulsifying agent in the form of a dispersed droplet phase in the viscous gel.

In an additional aspect, the invention provides a kit adapted to provide an injectable depot composition comprising as kit components: (a) a biocompatible polymer and a solvent that dissolves the polymer and forms a viscous gel; (b) emulsifying agent; and (c) beneficial agent.

BRIEF DESCRIPTION OF THE DRAWINGS

The foregoing and other objects, features and advantages of the present invention will be more readily understood upon reading the following detailed description in conjunction with the drawings in which.

DESCRIPTION OF THE PREFERRED EMBODIMENTS

Figure 1:
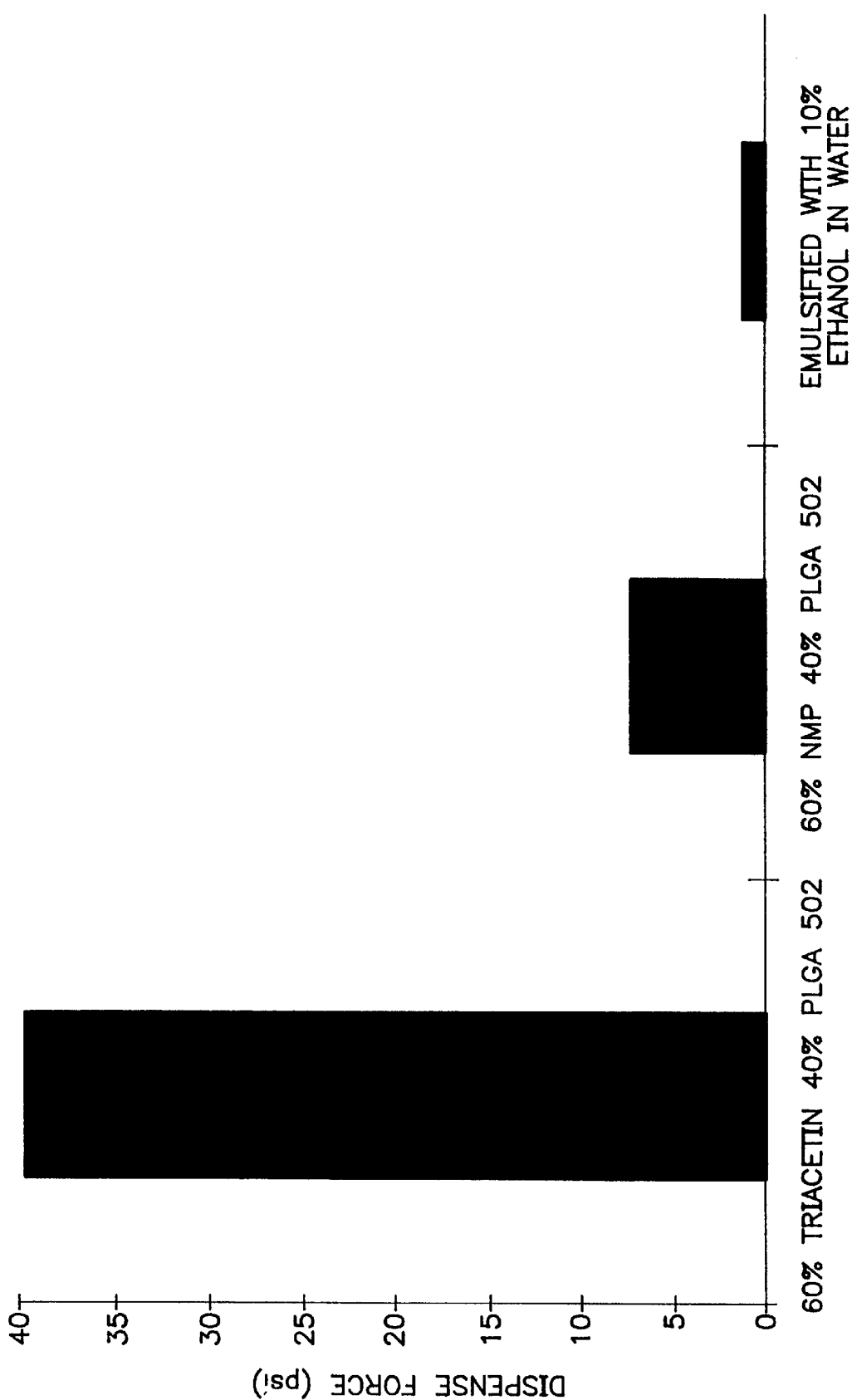
FIG. 1 is a graph illustrating the dispense force required to dispense the emulsified and non-emulsified viscous gel compositions through a 20 gauge needle in psig at 2 cc/min.

As explained above, one aspect of the present invention relates to an injectable depot gel composition comprising:

A) a biocompatible polymer;
B) a solvent that dissolves the biocompatible polymer and forms a viscous gel;
C) a beneficial agent; and
D) an emulsifying agent in the form of a dispersed droplet phase in the viscous gel.

The polymer, solvent and emulsifying agents of the invention must be biocompatible, that is they must not cause irritation or necrosis in the environment of use. The environment of use is a fluid environment and may comprise a subcutaneous or intramuscular portion or body cavity of a human or animal.

Polymers that may be useful in the invention may be biodegradable and may include, but are not limited to polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly (malic acid), poly(amino acids), polyvinylpyrrolidone, polyethylene glycol, polyhydroxycellulose, chitin, chitosan, and copolymers, terpolymers and mixtures thereof.

The polymer may be a polylactide, that is, a lactic acid-based polymer that can be based solely on lactic acid or can be a copolymer based on lactic acid and glycolic acid which may include small amounts of other comonomers that do not substantially affect the advantageous results which can be achieved in accordance with the present invention. As used herein, the term "lactic acid" includes the isomers L-lactic acid, D-lactic acid, DL-lactic acid and lactide while the term "glycolic acid" includes glycolide. The polymer may have a monomer ratio of lactic acid/glycolic acid of from about 100:0 to about 15:85, preferably from about 60:40 to about 75:25 and an especially useful copolymer has a monomer ratio of lactic acid/glycolic acid of about 50:50.

The lactic acid-based polymer has a number average molecular weight of from about 1,000 to about 120,000, preferably from about 10,000 to about 30,000 as determined by gas phase chromatography. As indicated in aforementioned U.S. Pat. No. 5,242,910, the polymer can be prepared in accordance with the teachings of U.S. Pat. No. 4,443,340. Alternatively, the lactic acid-based polymer can be prepared directly from lactic acid or a mixture of lactic acid and glycolic acid (with or without a further comonomer) in accordance with the techniques set forth in U.S. Pat. No. 5,310,865. The contents of all of these patents are incorporated by reference. Suitable lactic acid-based polymers are available commercially. For instance, 50:50 lactic acid:glycolic acid copolymers having molecular weights of 10,000, 30,000 and 100,000 are available from Boehringer Ingelheim (Petersburg, Va.).

The biocompatible polymer is present in the composition in an amount ranging from about 5 to about 80% by weight, preferably from about 20 to about 50% by weight and often 35 to 45% by weight of the viscous gel, the viscous gel comprising the combined amounts of the biocompatible polymer and the solvent. Once in place in the environment of use, the solvent will diffuse slowly away from the depot and the polymer will slowly degrade by hydrolysis.

The solvent must be biocompatible and is selected so as to dissolve the polymer to form a viscous gel that can maintain particles of the beneficial agent dissolved or dispersed and isolated from the environment of use prior to release. Illustrative solvents which can be used in the present invention include but are not limited to triacetin, N-methyl-2-pyrrolidone, 2-pyrrolidone, glycerol formal, methyl acetate, benzyl benzoate, ethyl acetate, methyl ethyl ketone, dimethylformamide, dimethyl sulfoxide, tetrahydrofuran, caprolactam, decylmethylsulfoxide, oleic acid, and 1-dodecylazacyclo-heptan-2-one and mixtures thereof. The preferred solvents are triacetin and N-methyl-2-pyrrolidone. Triacetin provides a high level of polymer dissolution which leads to greater gel viscosities, with attendant higher force needed to dispense the viscous gel when compared with other solvents. These characteristics enable the beneficial agent to be maintained without exhibiting a burst effect, but make it difficult to dispense the gel through a needle. For instance, as shown in FIG. 1, a gel prepared from 40% by weight of a 50:50 lactic acid:glycolic polymer and 60% by weight of triacetin required about 40 psig to dispense the gel through a standard 20 gauge needle at 2 cc/min while a gel prepared from the same amount of polymer with 60% by weight of N-methyl-2-pyrrolidone required only about 8 psig. FIG. 1 further shows that when the emulsifying agent (in this case 33% by weight of a 10% ethanol solution) is added to the viscous gel according to the invention, the dispense force needed is only about 2 psig. The shear thinning characteristics of the depot gel compositions of the present invention allow them be readily injected into an animal including humans using standard gauge needles without requiring undue dispensing pressure.

The solvent is typically present in an amount of from about 95 to about 20% by weight and is preferably present in an amount of from about 80 to about 50% by weight and often 65 to 55% by weight of the viscous gel, that is the combined amounts of the polymer and the solvent. The viscous gel formed by mixing the polymer and the solvent typically exhibits a viscosity of from about 1,000 to about 200,000 poise, preferably from about 5 to about 50,000 poise measured at a 1.0 sec$^{-1}$ shear rate and 25° C. using a Haake Viscometer at about 1–2 days after mixing is completed. Mixing the polymer with the solvent can be achieved with conventional low shear equipment such as a Ross double planetary mixer for from about 1 to about 2 hours.

The beneficial agent can be any physiologically or pharmacologically active substance or substances optionally in combination with pharmaceutically acceptable carriers and additional ingredients such as antioxidants, stabilizing agents, permeation enhancers, etc. that do not substantially adversely affect the advantageous results that can be attained by the present invention. The beneficial agent may be any of the agents which are known to be delivered to the body of a human or an animal and that are preferentially soluble in water rather than in the polymer-dissolving solvent. These agents include drug agents, medicaments, vitamins, nutrients, or the like. Included among the types of agents which meet this description are nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, antiinflammatory corticosteroids, ocular drugs and synthetic analogs of these species.

Examples of drugs which may be delivered by the composition of the present invention include, but are not limited to prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, bone morphogenic proteins, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandins, fertility promoters, growth factors, coagultion factors, human pancreas hormone releasing factor, analogs and derivatives of these compounds, and pharmaceutically acceptable salts of these compounds, or their analogs or derivatives.

To the extent not mentioned in the previous paragraph, the beneficial agents described in aforementioned U.S. Pat. No. 5,242,910 can also be used. One particular advantage of the present invention is that materials, such as proteins, as exemplified by the enzyme lysozyme, and cDNA, and DNA incorporated into vectors both viral and nonviral, which are difficult to microcapsulate or process into microspheres can be incorporated into the compositions of the present invention without the level of degradation experienced with other techniques.

The beneficial agent is preferably incorporated into the viscous gel formed from the polymer and the solvent in the form of particles typically having an average particle size of from about 0.1 to about 100 microns, preferably from about 1 to about 25 microns and often from 2 to 10 microns. For instance, particles having an average particle size of about 5 microns have been produced by spray drying or spray freezing an aqueous mixture containing 50% sucrose and 50% chicken lysozyme (on a dry weight basis). Such particles have been used in certain of the examples illustrated in the figures.

To form a suspension of particles of the beneficial agent in the viscous gel formed from the polymer and the solvent, any conventional low shear device can be used such as a Ross double planetary mixer at ambient conditions. In this manner, efficient distribution of the beneficial agent can be achieved substantially without degrading the beneficial agent.

The beneficial agent is typically dissolved or dispersed in the composition in an amount of from about 1 to about 50% by weight, preferably in an amount of from about 5 to about 25% and often 10 to 20% by weight of the combined amounts of the polymer, solvent and beneficial agent. Depending on the amount of beneficial agent present in the composition, one can obtain different release profiles. More specifically, for a given polymer and solvent, by adjusting the amounts of these components and the amount of the beneficial agent, one can obtain a release profile that depends more on the degradation of the polymer than the diffusion of the beneficial agent from the composition or vice versa. In this respect, at lower beneficial agent loading rates, one generally obtains a release profile reflecting degradation of the polymer wherein the release rate increases with time. At higher loading rates, one generally obtains a release profile caused by diffusion of the beneficial agent wherein the release rate decreases with time. At intermediate loading rates, one obtains combined release profiles so that if desired, a substantially constant release rate can be attained. While the particular release rate depends on the particular circumstances, such as the beneficial agent to be administered, release rates on the order of from about 1 to about 10 micrograms/day for periods of from about 7 to about 90 days can be obtained. Further, the dose of beneficial agent may be adjusted by adjusting the amount of injectable depot gel injected. As will be apparent from the following results, one can avoid a burst effect and administer on the order of 1% by weight of the beneficial agent in the composition during the first day.

Figure 2:
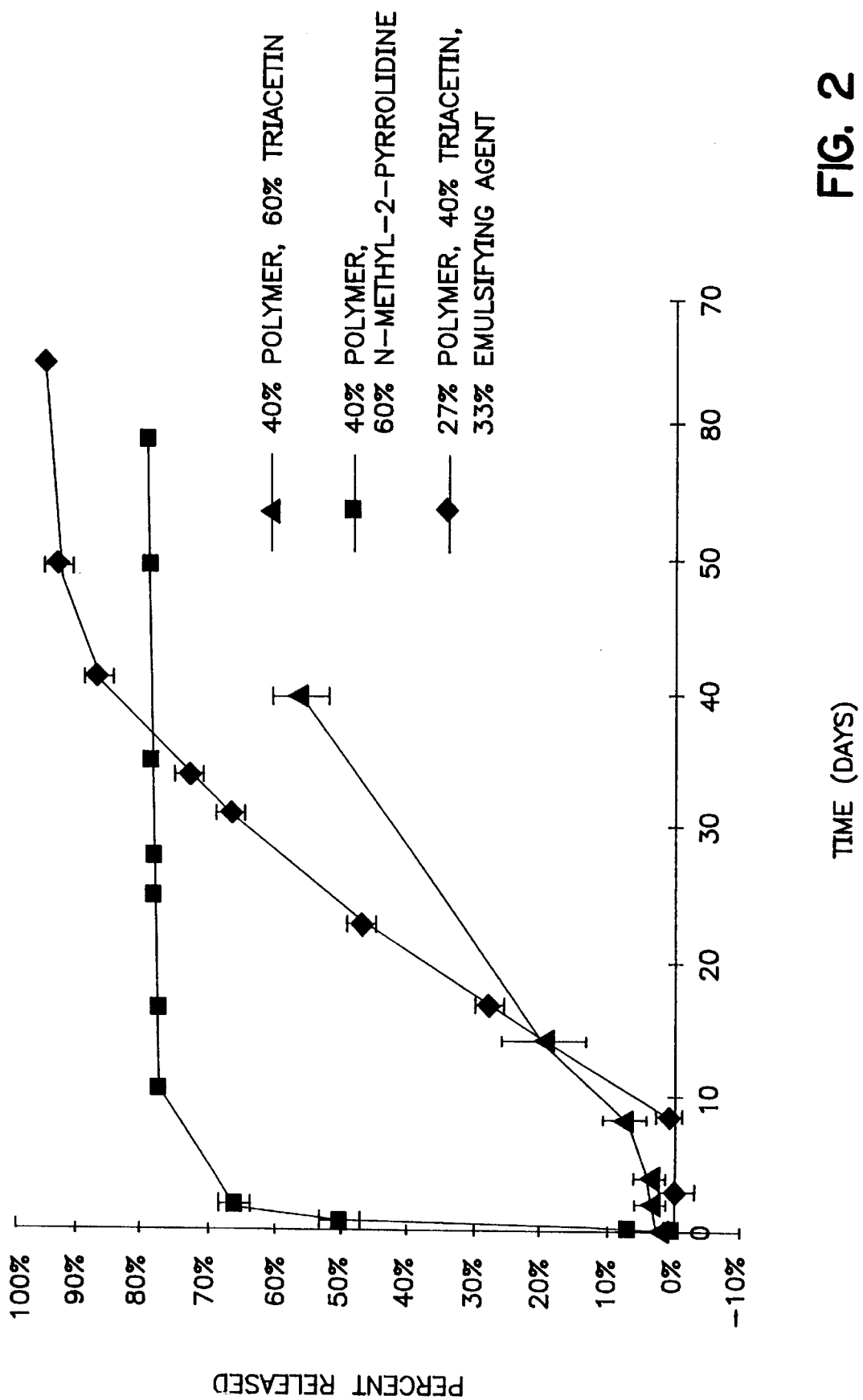
FIG. 2 is a graph illustrating the release profiles of lysozyme from three different compositions in days.

FIG. 2 shows the release rates obtained from the compositions described with regard to FIG. 1. The gel prepared from 40% by weight of a 50:50 lactic acid:glycolic polymer and 60% by weight triacetin is thick and thus difficult to inject but shows little burst (less than 2% of the beneficial agent is delivered in the first eight days). The gel prepared from 40% by weight of a 50:50 lactic acid:glycolic polymer and 60% by weight N-methyl-2-pyrrolidone is thin and injectable but shows a large burst (greater than 70% of the beneficial agent is delivered in the first eight days). The gel prepared from 27% by weight of a 50:50 lactic acid:glycolic polymer, 40% by weight triacetin and 33% by weight of a 10% ethanol, 90% isotonic saline solution is thin and injectable and shows little burst (less than 10% of the beneficial agent is delivered in the first eight days). In each case, lysozyme is the beneficial agent and comprises 20% by weight of the combined beneficial agent, polymer and solvent formulation.

The emulsifying agent constitutes an important aspect of the present invention. When the emulsifying agent is mixed with the viscous gel formed from the polymer and the solvent using conventional static or mechanical mixing devices, such as an orifice mixer, the emulsifying agent forms a separate phase composed of dispersed droplets of microscopic size that typically have an average diameter of less than about 100 microns. The continuous phase is formed of the polymer and the solvent. The particles of the beneficial agent may be dissolved or dispersed in either the continuous phase or the droplet phase. In the resulting thixotropic composition, the droplets of emulsifying agent elongate in the direction of shear and substantially decrease the viscosity of the viscous gel formed from the polymer and the solvent. For instance, with a viscous gel having a viscosity of from about 5,000 to about 50,000 poise measured at 1.0 sec$^{-1}$ at 25° C., one can obtain a reduction in viscosity to less than 100 poise when emulsified with a 10% ethanol/water solution at 25° C. as determined by Haake rheometer. Because dispersion and dissolution of the particles of beneficial agent in the emulsifying agent proceeds more rapidly than does dissolution or dispersion of the beneficial agent in the viscous polymer, the beneficial agent can be mixed with the emulsifying agent just prior to the time of use. This permits the beneficial agent to be maintained in a dry state prior to use, which may be advantageous in those instances where long term stability of the beneficial agent in the viscous gel is of concern. Additionally, since the beneficial agent will remain in the droplet phase that is entrapped within the viscous gel as it forms, it is possible to select an emulsifying agent in which the drug is optimally stable and thus prolong stability of the beneficial agent in the gel composition. An added benefit is the opportunity to program the release of beneficial agent via diffusion through the porous structure of the implant, rather than by degradation and dissolution of the polymer structure.

When dissolution or dispersion of the beneficial agent in the emulsifying agent is intended, the injectable depot of this invention may be provided as a kit, having kit components comprising (a) a mixture of polymer and solvent, (b) emulsifying agent and (c) beneficial agent. Prior to use the beneficial agent is mixed with the emulsifying agent, and that solution or suspension is mixed with the polymer/solvent mixture to prepare the injectable depot implant for use.

The emulsifying agent is present in an amount ranging from about 5 to about 80%, preferably from about 20 to about 60% and often 30 to 50% by weight based on the amount of the injectable depot gel composition, that is the combined amounts of polymer, solvent, emulsifying agent and beneficial agent. Illustrative emulsifying agents are water, alcohols, polyols, esters, carboxylic acids, ketones, aldehydes and mixtures thereof. Preferred emulsifying agents are alcohols, propylene glycol, ethylene glycol, glycerol, water, and solutions and mixtures thereof. Especially preferred are water, ethanol, and isopropyl alcohol and solutions and mixtures thereof. The type of emulsifying agent affects the size of the dispersed droplets. For instance, ethanol will provide droplets that have average diameters that can be on the order of ten times larger than the droplets obtained with an isotonic saline solution containing 0.9% by weight of sodium chloride at 21° C.

While normally no other components are present in the composition, to the extent that conventional optional ingredients are desired, such as polyethylene glycol, hydroscopic agents, stabilizing agents and others, they are used in an amount that does not substantially affect the advantageous results which can be attained in accordance with the present invention.

Figure 3:
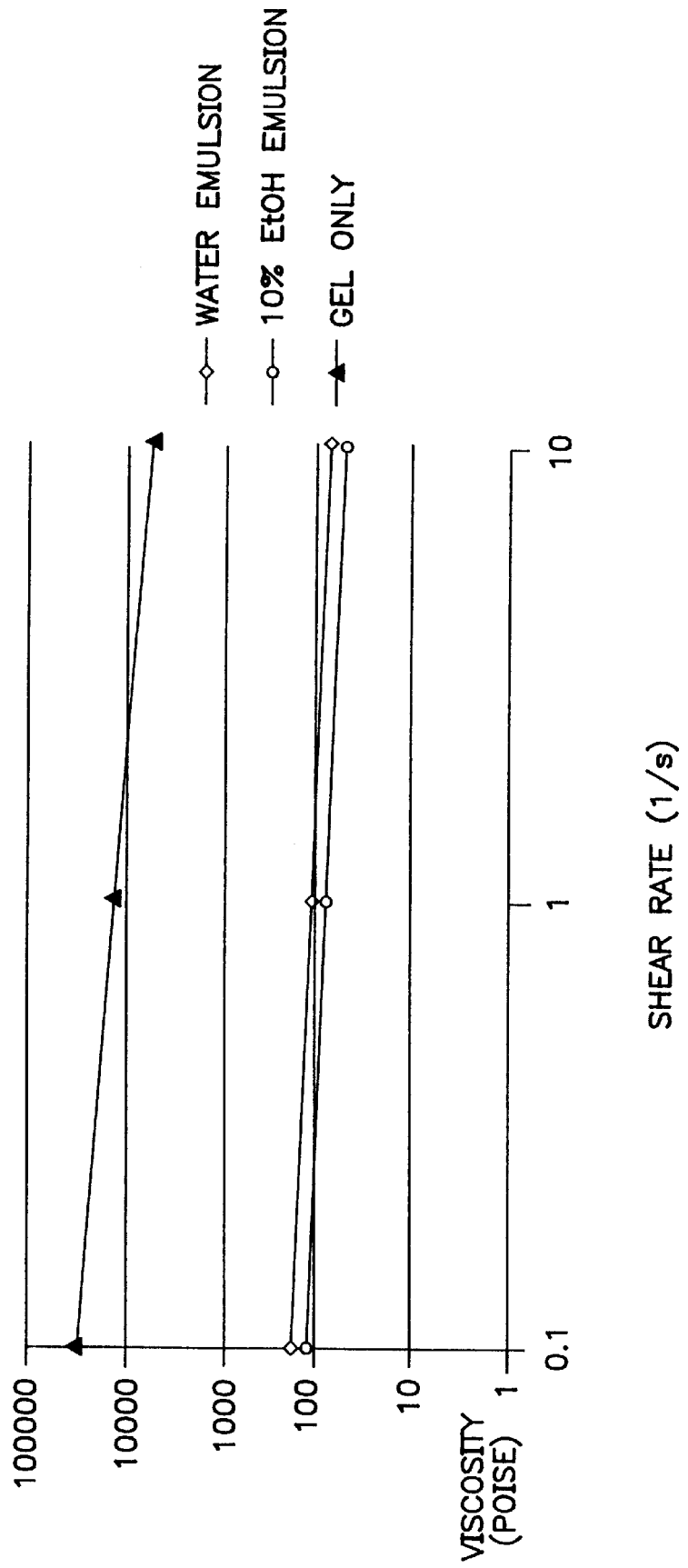
FIG. 3 is a graph illustrating the viscosity profiles at different shear rates of water alone and of an aqueous mixture of ethanol, and of the viscous gel without emulsifying agent.

To illustrate various aspects of the invention further, FIG. 3 shows the viscosities at different shear rates using water alone and an aqueous mixture containing 10% by volume of ethanol at a weight ratio of 2:1 (gel:emulsifying agent) using a viscous gel formed from 50% by weight of a 50:50 lactic acid:glycolic acid copolymer and 50% by weight of triacetin compared to the viscosities of the viscous gel without emulsifying agent.

It is to be understood that the emulsifying agent of the present invention does not constitute a mere diluent that reduces viscosity by simply decreasing the concentration of the components of the composition. The use of conventional diluents can reduce viscosity, but can also cause the burst effect mentioned previously when the diluted composition is injected. In contrast, the injectable depot composition of the present invention can be formulated to avoid the burst effect by selecting the emulsifying agent so that once injected into place, the emulsifying agent has little impact on the release properties of the original system. Further compositions without beneficial agent may be useful for wound healing, bone repair and other structural support purposes.

To further understand the various aspects of the present invention, the results set forth in the previously described Figures were obtained in accordance with the following examples.

EXAMPLE 1

Lysozyme particles were made by spray drying 50% sucrose and 50% chicken lysozyme (on a dry weight basis).

A viscous gel material was prepared by heating 60% by weight of triacetin with 40% by weight of a 50:50 lactic acid:glycolic acid copolymer to 37° C. overnight. The viscous gel was allowed to cool to room temperature while mixing continued. The lysozyme particles were added to the viscous gel in a ratio of 20:80 lysozyme particles:gel (by weight). The combination was mixed for 5 minutes. Immediately prior to use, a 10% ethanol, 90% isotonic saline solution was added as the emulsifying agent. The emulsifying agent comprised ⅓ of the total injectable depot gel composition. 0.5 grams of this injectable depot composition was then injected into a rat.

EXAMPLE 2

A viscous gel material is prepared by heating 60% by weight of triacetin with 40% by weight of a 50:50 lactic acid:glycolic acid copolymer to 37° C. overnight. The viscous gel is allowed to cool to room temperature while mixing is continued. Immediately prior to use, lysozyme particles, prepared as in Example 1 and in the same amount, are combined with a 10% ethanol, 90% isotonic saline solution, as an emulsifying agent, in the amount used in Example 1. The emulsifying agent-lysozyme solution is mixed with the amount of gel material used in Example 1 to form an injectable depot gel composition. The fabricated injectable depot gel composition is suitable for injection into an animal.

In accordance with various aspects of the present invention, one or more significant advantages can be obtained. More specifically, using simple processing steps, one can obtain a depot gel composition that can be injected into place in an animal without surgery using a low dispensing force through standard needles. Once in place, the composition will quickly return to its original viscosity and may exhibit rapid hardening so as to substantially avoid a burst effect and provide the desired beneficial agent release profile. Furthermore, once the beneficial agent has been fully administered, there is no need to remove the composition since it is fully biodegradable. As a still further advantage, the present invention avoids the use of microparticle or microcapsulation techniques which can degrade certain beneficial agents, like peptide and nucleic acid-based drugs and which microparticles and microcapsules maybe difficult to remove from the environment of use. Since the viscous gel is formed without the need for water, temperature extremes, or other solvents, suspended particles of beneficial agent remain dry and in their original configuration, which contributes to the stability of thereof. Further, since a mass is formed, the injectable depot gel composition may be retrieved from the environment of use if desired.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims.

We claim:

1. An injectable depot gel composition comprising:
    a continuous, viscous gel phase comprising
        a biocompatible polymer and
        an organic solvent that dissolves the biocompatible polymer and forms a viscous gel;
    a beneficial agent; and a separate, droplet phase dispersed in the viscous gel phase comprising
        an emulsifying agent, whereby the depot gel composition is thixotropic.

2. The injectable gel depot composition of claim 1 wherein the biocompatible polymer is selected from the group consisting of polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, chitin, chitosan, and copolymers, terpolymers and mixtures thereof.

3. The injectable depot gel composition of claim 1 wherein the biocompatible polymer is a lactic acid-based polymer.

4. The injectable depot gel composition of claim 3 wherein the lactic acid-based polymer has a monomer ratio of lactic acid to glycolic acid in the range of 100:0 to about 15:85.

5. The injectable depot gel composition of claim 3 wherein the lactic acid-based polymer has a number average molecular weight of from 1,000 to 120,000.

6. The injectable depot gel composition of claim 1 wherein the solvent that can dissolve the biocompatible polymer to form a viscous gel is selected from the group consisting of triacetin, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacyclo-heptan-2-one and mixtures thereof.

7. The injectable depot gel composition of claim 1 wherein the solvent is selected from the group consisting of triacetin and N-methyl-2-pyrrolidone, and mixtures thereof.

8. The injectable depot gel composition of claim 1 wherein the solvent is triacetin.

9. The injectable depot gel composition of claim 1 wherein the polymer is present in an amount of from 5 to 80% by weight of the combined amounts of the polymer and the solvent.

10. The injectable depot gel composition of claim 1 wherein the solvent is present in an amount of from 95 to 20% by weight of the combined amounts of the polymer and the solvent.

11. The injectable depot gel composition of claim 1 wherein the viscous gel formed by the polymer and the solvent has a viscosity of from 1,000 to 200,000 poise.

12. The injectable depot gel composition of claim 1 wherein the beneficial agent is a drug.

13. The injectable depot gel composition of claim 1 wherein the beneficial agent is a peptide.

14. The injectable depot gel composition of claim 1 wherein the beneficial agent is a protein.

15. The injectable depot gel composition of claim 1 wherein the beneficial agent is growth hormone.

16. The injectable depot gel composition of claim 1 wherein the beneficial agent is present in an amount of from 1 to 50% by weight of the combined amounts of the polymer, the solvent and the beneficial agent.

17. The injectable depot gel composition of claim 1 wherein the beneficial agent is in the form of particles dispersed or dissolved in the viscous gel.

18. The injectable depot gel composition of claim 17 wherein the beneficial agent is in the form of particles having an average particle size of from 0.1 to 100 microns.

19. The injectable depot gel composition of claim 1 wherein the emulsifying agent is selected from the group consisting of water, alcohols, polyols, esters, carboxylic acids, ketones, aldehydes and mixtures thereof.

20. The injectable depot gel composition of claim 1 wherein the emulsifying agent is selected from the group consisting of alcohols, propylene glycol, ethylene glycol, glycerol, water and solutions and mixtures thereof.

21. The injectable depot gel composition of claim 1 wherein the emulsifying agent is selected from the group consisting of ethanol, isopropyl alcohol, water, solutions thereof, and mixtures thereof.

22. The injectable depot gel composition of claim 1 wherein the emulsifying agent is water.

23. The injectable depot gel composition of claim 1 wherein the emulsifying agent is present in an amount of from 5 to 80% by weight of the injectable depot gel composition.

24. A method of preparing an injectable depot gel composition comprising:
A) mixing a biocompatible polymer and an organic solvent whereby the solvent dissolves the polymer and forms a viscous gel as a continuous phase;
B) dispersing or dissolving a beneficial agent in the viscous gel to form a beneficial agent containing viscous gel; and
C) mixing an emulsifying agent with the beneficial agent containing viscous gel, thereby forming a separate, dispersed droplet phase of the emulsifying agent in the beneficial agent containing viscous gel to provide a thixotropic injectable depot gel composition.

25. A method of preparing an injectable depot gel composition comprising:
A) mixing a biocompatible polymer and an organic solvent whereby the solvent dissolves the polymer to form a viscous gel as a continuous phase;
B) dispersing or dissolving a beneficial agent in an emulsifying agent to form a beneficial agent containing emulsifying agent; and
C) mixing the beneficial agent containing emulsifying agent with the viscous gel to form a separate, dispersed droplet phase of the beneficial agent containing emulsifying agent in the viscous gel and provide a thixotropic injectable depot gel composition.

26. An injectable depot gel composition comprising:
a continuous, viscous, gel phase comprising
a biocompatible polymer and
an organic solvent that dissolves the polymer and forms a viscous gel; and a separate, droplet phase dispersed in the viscous gel phase comprising
an emulsifying agent, whereby the depot gel composition is thixotropic.

27. A kit adapted to provide a thixotropic injectable depot composition having a continuous phase formed as a viscous polymer-solvent gel in which an emulsifying agent is present in the form of a dispersed droplet phase, comprising as kit components: (a) a biocompatible polymer and an organic solvent that dissolves the polymer and forms a viscous gel; (b) emulsifying agent; and (c) beneficial agent dispersible or dissolvable in the emulsifying agent.

* * * * *